US012796967B2

(12) United States Patent
Fu et al.

(10) Patent No.: US 12,796,967 B2
(45) Date of Patent: Nov. 17, 2026

(54) MACHINE VISION-BASED METHOD AND SYSTEM FOR DETERMINING A RANGE OF MOTION OF A JOINT OF A HAND OF A SUBJECT

(71) Applicants: The Education University of Hong Kong, Hong Kong (HK); Wuxi Ninth People's Hospital Affiliated to Soochow University, Wuxi City (CN)

(72) Inventors: Hong Fu, Hong Kong (HK); Yan Wen Xu, Wuxi City (CN); Beibei Hou, Hong Kong (HK); Jun Wang, Wuxi City (CN); Ying Wang, Wuxi City (CN); Che Hin Chetwyn Chan, Hong Kong (HK)

(73) Assignees: The Education University of Hong Kong, Hong Kong (HK); Wuxi Ninth People's Hospital Affiliated to Soochow University, Wuxi city (CN)

( * ) Notice: Subject to any disclaimer, the term of this patent is extended or adjusted under 35 U.S.C. 154(b) by 348 days.

(21) Appl. No.: 18/399,471

(22) Filed: Dec. 28, 2023

(65) Prior Publication Data

US 2025/0213141 A1 Jul. 3, 2025

(51) Int. Cl.
*A61B 5/11* (2006.01)
*G06T 7/285* (2017.01)
*G06T 7/80* (2017.01)

(52) U.S. Cl.
CPC ............ *A61B 5/1124* (2013.01); *G06T 7/285* (2017.01); *G06T 7/80* (2017.01)

(58) Field of Classification Search
CPC ....... A61B 5/1124; A61B 5/1121; G06T 7/80; G06T 7/285; G06V 40/28
See application file for complete search history.

(56) References Cited

U.S. PATENT DOCUMENTS 10,849,532 B1 12/2020 Santello et al.
2015/0341618 A1* 11/2015 He ........................ G06T 7/0012 348/47

FOREIGN PATENT DOCUMENTS

CN 106355598 A 1/2017
CN 108537203 A 9/2018
(Continued)

OTHER PUBLICATIONS

Nizamis, Kostas, et al. "A novel setup and protocol to measure the range of motion of the wrist and the hand." Sensors 18.10 (2018): 3230. (Year: 2018).*
(Continued)

*Primary Examiner* — Eric J Messersmith
(74) *Attorney, Agent, or Firm* — IDEA Intellectual Limited; Sam T. Yip

(57) ABSTRACT

The present disclosure provides a machine vision-based method for determining a range of motion of a joint of a hand of a subject and a system for implementing the same. The provided method comprises: facilitating the subject to perform a hand movement at a preset position; capturing at least two prior-movement images of the hand when the hand is in a neutral posture before performing the hand movement; capturing at least two post-movement images of the hand when the hand is in an assessment posture after performing the hand movement; processing the captured prior-movement images to obtain a plurality of prior-movement key point positions; processing the captured post-movement images to obtain a plurality of post-movement key point positions; and calculating the range of motion of the joint based on the plurality of prior-movement key point positions and the plurality of post-movement key point positions.

3 Claims, 7 Drawing Sheets

(56) References Cited

FOREIGN PATENT DOCUMENTS

| | | | |
|---|---|---|---|
| CN | 109977791 | A | 7/2019 |
| CN | 116844188 | A | 10/2023 |
| CN | 116959704 | A | 10/2023 |
| CN | 116997941 | A | 11/2023 |
| KR | 102566211 | B1 | 8/2023 |

OTHER PUBLICATIONS

Lisa Reissner et al., Minimal detectable difference of the finger and wrist range of motion: Comparison of goniometry and 3D motion analysis, Journal of Orthopaedic Surgery and Research, 2019, vol. 14, No. 173, p. 1-10.
Trieu Pham et al., A Non-Contact Measurement System for the Range of Motion of the Hand, Sensors, 2015, vol. 15, No. 8, p. 18315-18333.
Luciano Walenty Xavier Cejnog et al., A framework for automatic hand range of motion evaluation of rheumatoid arthritis patients, Informatics in Medicine Unlocked, 2021, vol. 23, No. 100544, p. 1-12.
Search Report of the corresponding Hong Kong Short-term Patent Application No. 32023084756.0 mailed on Jan. 23, 2024.

* cited by examiner

MACHINE VISION-BASED METHOD AND SYSTEM FOR DETERMINING A RANGE OF MOTION OF A JOINT OF A HAND OF A SUBJECT

FIELD OF THE INVENTION

The present invention generally relates to hand function assessment. More specifically, the present invention relates to a machine vision-based method for determining the range of motion of the joints of a hand of a subject and a system for implementing the same.

BACKGROUND OF THE INVENTION

The hand is one of the most complex and versatile anatomical structures of the human appendages. It serves a crucial function for interacting with the external environment and plays a significant role in human life. Functional disorders of the hand can limit individual independence and affect the quality of life. The determination of range of motion (ROM) is an essential component of hand function assessment. In clinical settings, hand joint angle measurement methods are commonly used to obtain the ROM of hand joints for the following reasons. Firstly, hand joint angles reflect hand function and motor ability. By measuring hand joint angles, one can understand the ROM, flexibility, and coordination of the hand joints, aiding in the assessment of hand function recovery and the extent of damage. Secondly, measuring hand joint angles can provide important evidence for clinical diagnosis and assist in rehabilitation therapy. Joint angle measurements help physicians quickly locate the site of lesions, determine the degree of damage, and formulate appropriate treatment plans. Lastly, in the field of medicine and sports science, hand joint measurements can reveal the dynamic characteristics and movement patterns of hand motion. This is crucial for understanding the biomechanical features of hand motion, optimizing motor skills, and improving sports training techniques.

Medical professionals often use universal goniometers or inclinometers to manually measure the declination angles of finger joints to assess the joint movement range. However, one significant challenge in manual assessment is intra- and inter-rater reliability. The methods involving manual assessment are also inefficient and expensive. In other approaches, electronic wearable devices were introduced to sense the hand movement. However, one of the challenges in these approaches is that the wearable devices require physical contact with the finger to achieve the best accuracy. Injuries, such as burns, wounds, lacerations or even dermatological conditions, can cause difficulties in conducting the measurement.

Adapting optical measurement systems or computer vision-based approaches provides a non-contact form of measurement. For example, Chinese patent application publication no. CN106355598A disclosed an automatic wrist and finger joint motion degree measurement method based on Kinect depth images. It is still desirable to have a more versatile vision-based hand joint angle measurement system which can measure hand joint angle for various hand movements and provide a more comprehensive hand function assessment.

SUMMARY OF THE INVENTION

According to one aspect of the present invention, a machine vision-based method for determining the range of motion of the joints of a hand of a subject is provided. The provided method comprises: facilitating the subject to perform a hand movement at a preset position; capturing at least two prior-movement images of the hand when the hand is in a neutral posture before performing the hand movement; capturing at least two post-movement images of the hand when the hand is in an assessment posture after performing the hand movement; processing the captured prior-movement images to obtain a plurality of prior-movement key point positions; processing the captured post-movement images to obtain a plurality of post-movement key point positions; and calculating the range of motion of the joint based on the plurality of prior-movement key point positions and the plurality of post-movement key point positions.

According to another aspect of the present invention, a machine vision-based system for determining a ROM of a joint of a hand of a subject is provided. The provided system comprises: a supporter configured to facilitate the subject to perform a hand movement at a preset position; at least two cameras configured to: capture at least two prior-movement images of the hand when the hand is in a neutral posture before performing the hand movement; and capture at least two post-movement images of the hand when the hand is in an assessment posture after performing the hand movement; and a processor configured to: process the captured prior-movement images to obtain a plurality of prior-movement key point positions; process the captured post-movement images to obtain a plurality of post-movement key point positions; an calculate the range of motion of the joint based on the plurality of prior-movement key point positions and the plurality of post-movement key point positions.

According to a further aspect of the present invention, a non-transitory computer-readable storage medium is provided to store a program including instructions for performing a machine vision-based method for determining a range of motion of a joint of a hand of a subject. The method comprises: facilitating the subject to perform a hand movement at a preset position; capturing at least two prior-movement images of the hand when the hand is in a neutral posture before performing the hand movement; capturing at least two post-movement images of the hand when the hand is in an assessment posture after performing the hand movement; processing the captured prior-movement images to obtain a plurality of prior-movement key point positions; processing the captured post-movement images to obtain a plurality of post-movement key point positions; and calculating the range of motion of the joint based on the plurality of prior-movement key point positions and the plurality of post-movement key point positions.

The present invention introduces an unconstrained and non-invasive machine vision-based approach, eliminating the need for direct hand contact. Unlike conventional manual measurement techniques, the present invention prevents human biases, reducing errors for more dependable results. The provided measurement method expedites hand joint angle measurements while concurrently assessing multiple hand joints. This efficiency not only saves time and resources but also facilitates comprehensive hand mobility assessments. It preserves the natural fluidity of movement by enabling unrestricted hand motion, setting it apart from wearables, gloves, or external devices. The machine vision technology closely mimics real hand activity, enhancing measurement authenticity and accuracy.

The invention also offers timely rehabilitation progress feedback, aiding therapy efforts. Furthermore, its automated data processing generates detailed angle ranges, statistical insights, and visual representations, simplifying data interpretation and analysis for healthcare professionals. It also offers automated tracking of finger and upper limb movements, delivering precise measurements and insights into an individual's fine motor skills. This capability proves invaluable for therapists assessing patient recovery and evaluating fine motor skills in professions that demand such precision. Beyond its immediate applications, this advancement holds significant promise for research in biomechanics, neuroscience, and human-computer interaction.

BRIEF DESCRIPTION OF THE DRAWINGS

Aspects of the present disclosure may be readily understood from the following detailed description with reference to the accompanying figures. The illustrations may not necessarily be drawn to scale. That is, the dimensions of the various features may be arbitrarily increased or reduced for clarity of discussion. There may be distinctions between the artistic renditions in the present disclosure and the actual apparatus due to manufacturing processes and tolerances. Common reference numerals may be used throughout the drawings and the detailed description to indicate the same or similar components.

DETAILED DESCRIPTION

In the following description, preferred examples of the present invention will be set forth as embodiments which are to be regarded as illustrative rather than restrictive. Specific details may be omitted so as not to obscure the present disclosure; however, the disclosure is written to enable one skilled in the art to practice the teachings herein without undue experimentation.

Figure 1:
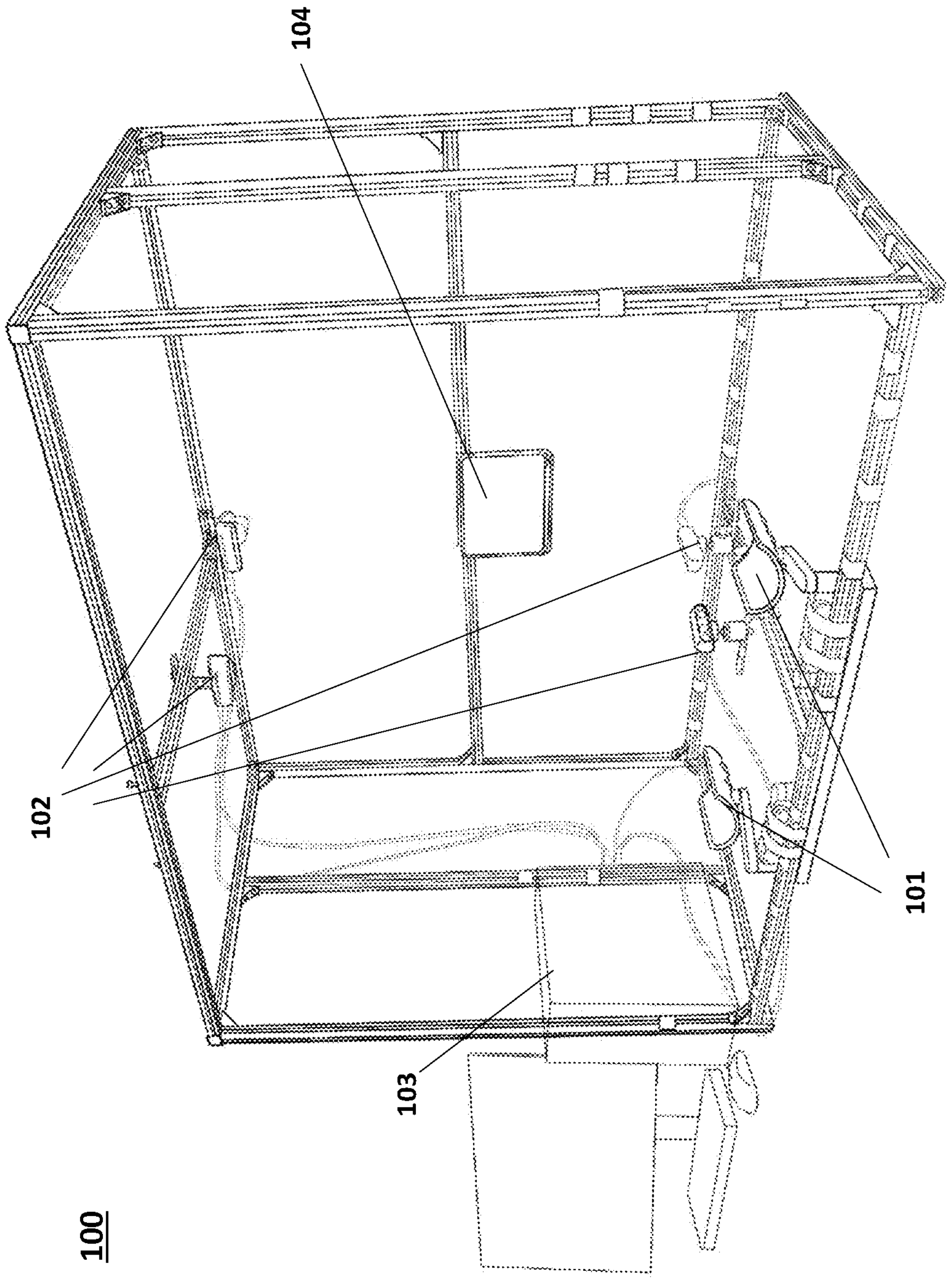
FIG. 1 shows a simplified diagram of a machine vision-based system for determining a range of motions of joints of a hand of a subject in accordance with one embodiment of the present invention.

Referring to FIG. 1 for the following description. In accordance with one embodiment of the present invention, a machine vision-based system 100 for determining a range of motions of joints of a hand of a subject. The system 100 comprises a hand supporter 101, two or more cameras 102 and a processor.

The hand supporter 101 is configured to support hands of the subject to facilitate the subject to perform a hand movement at a preset position.

The two or more cameras 102 are configured to capture images of the hand from two or more perspectives respectively. More specifically, the cameras 102 may be configured to: capture prior-movement images of the hand when the hand is in a neutral posture before performing the hand movement; and capture post-movement images of the hand when the hand has an assessment posture after performing the hand movement.

In some embodiments, each camera may be calibrated with respect to a three-dimensional space to obtain a respective camera projection matrix for reconstructing the 3D coordinates of joints from the 2D pixel coordinates in the image.

The camera projection matrix is a representation of the projecting points in the 3D space onto the pixel coordinate system. The process of projecting points in the 3D space onto the pixel coordinate system essentially involves taking global coordinates of a 3D point P $(X_w, Y_w, Z_w)$, mapping them using the pinhole imaging principle to the 2D image coordinate system, and applying rigid body transformation to convert them into 2D pixel coordinates p(u,v) in the image. The mathematical expression for the transformation is as follows:

$$\begin{bmatrix} u \\ v \\ 1 \end{bmatrix} = K[R \;\; t]\begin{bmatrix} X_w \\ Y_w \\ Z_w \\ 1 \end{bmatrix},$$

where R and t are the rotation matrix and translation vector of the camera with respect to the global coordinate system, which are known as extrinsic parameters of the camera. K is a matrix representing intrinsic parameters of the camera.

$$K = \begin{bmatrix} \frac{f}{d_x} & 0 & u_0 \\ 0 & \frac{f}{d_y} & v_0 \\ 0 & 0 & 1 \end{bmatrix}.$$

The camera projection matrix P is given by: P=K[R t].

The camera calibration is then a task of determining the camera projection matrix P given the global coordinates (X,Y,Z) of some 3D points and their corresponding image pixel coordinates (u,v), which are denoted as:

$$\begin{bmatrix} u_i \\ v_i \\ 1 \end{bmatrix} = P\begin{bmatrix} X_i \\ Y_i \\ Z_i \\ 1 \end{bmatrix}$$

Each pair of 2D and 3D counterpart points provides two linear equations about the camera projection matrix P, that is, n pairs of 2D and 3D counterpart points provide 2n linear equations. When n is greater than or equal to 6, a direct linear transformation can be used to solve this problem. Therefore, the camera projection matrix can be obtained through capturing an image with at least 6 non-coplanar 2D and 3D counterpart points.

The processor 103 is configured to process the captured images and calculate the range of motion of the joint of the hand. More specifically, the processor 103 may be configured to: process the captured prior-movement images to obtain a plurality of prior-movement key point positions; process the captured post-movement images to obtain a plurality of post-movement key point positions; and calculate the range of motion of the joint based on the plurality of prior-movement key point positions and the plurality of post-movement key point positions.

Preferably, the machine vision-based system 100 further comprises a display 104 configured to demonstrate the hand movement to the subject.

Figure 2:
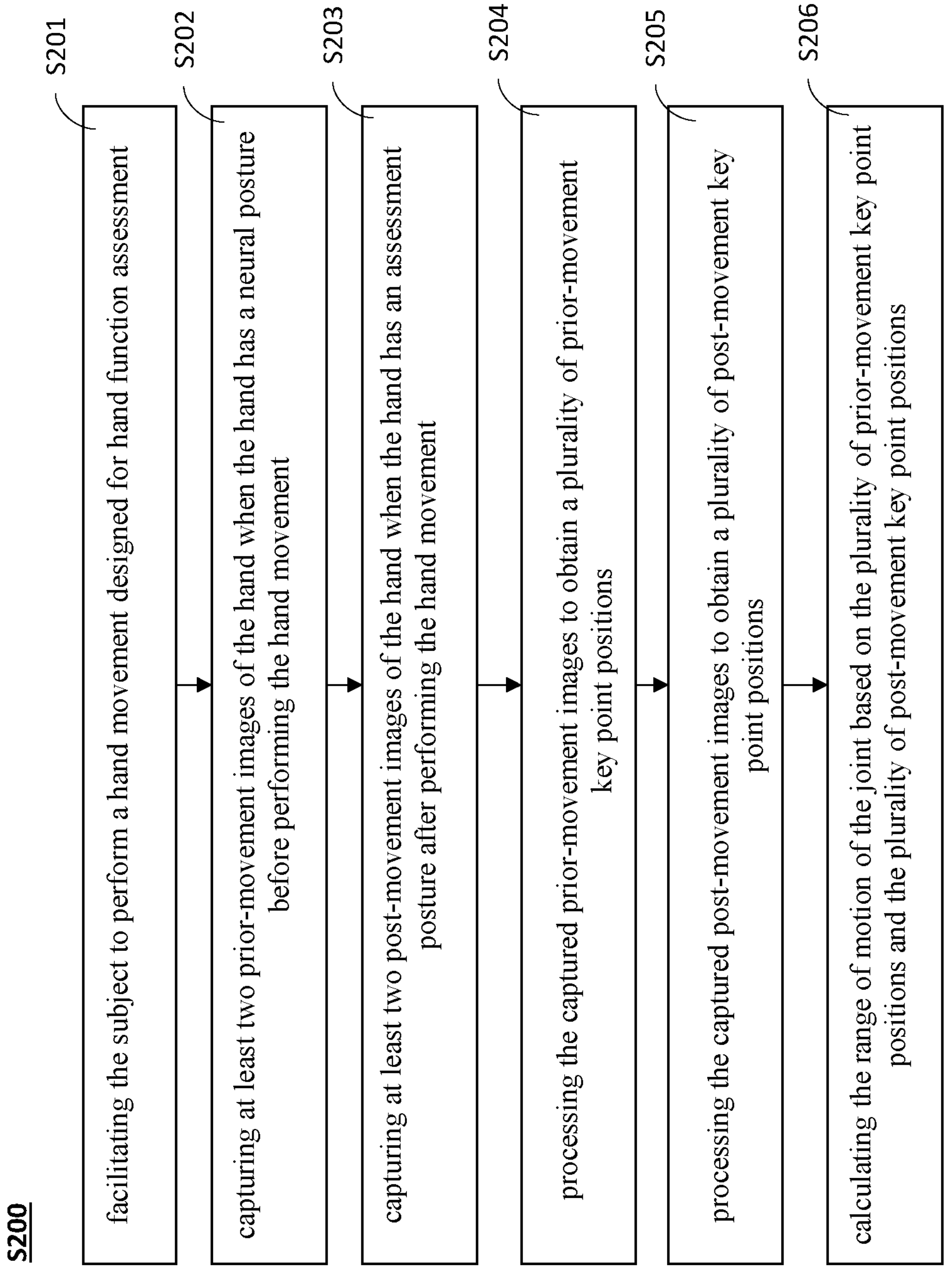
FIG. 2 shows a flow chart of a machine vision-based method for determining a range of motions of joints of a hand of a subject in accordance with one embodiment of the present invention.

Referring to FIG. 2 for the following description. In accordance with one embodiment of the present invention, a machine vision-based method S200 is provided for determining a range of motions of joints of a hand of a subject. The machine vision-based method S200 comprises:

- S101: facilitating the subject to perform a hand movement designed for hand function assessment;
- S102: capturing at least two prior-movement images of the hand when the hand has a neutral posture before performing the hand movement;
- S103: capturing at least two post-movement images of the hand when the hand has an assessment posture after performing the hand movement;
- S104: processing, using a neural network, the captured prior-movement images to obtain a plurality of prior-movement key point positions;
- S105: processing, using the neural network, the captured post-movement images to obtain a plurality of post-movement key point positions;
- S106: calculating the range of motion of the joint based on the plurality of prior-movement key point positions and the plurality of post-movement key point positions.

Figure 3:
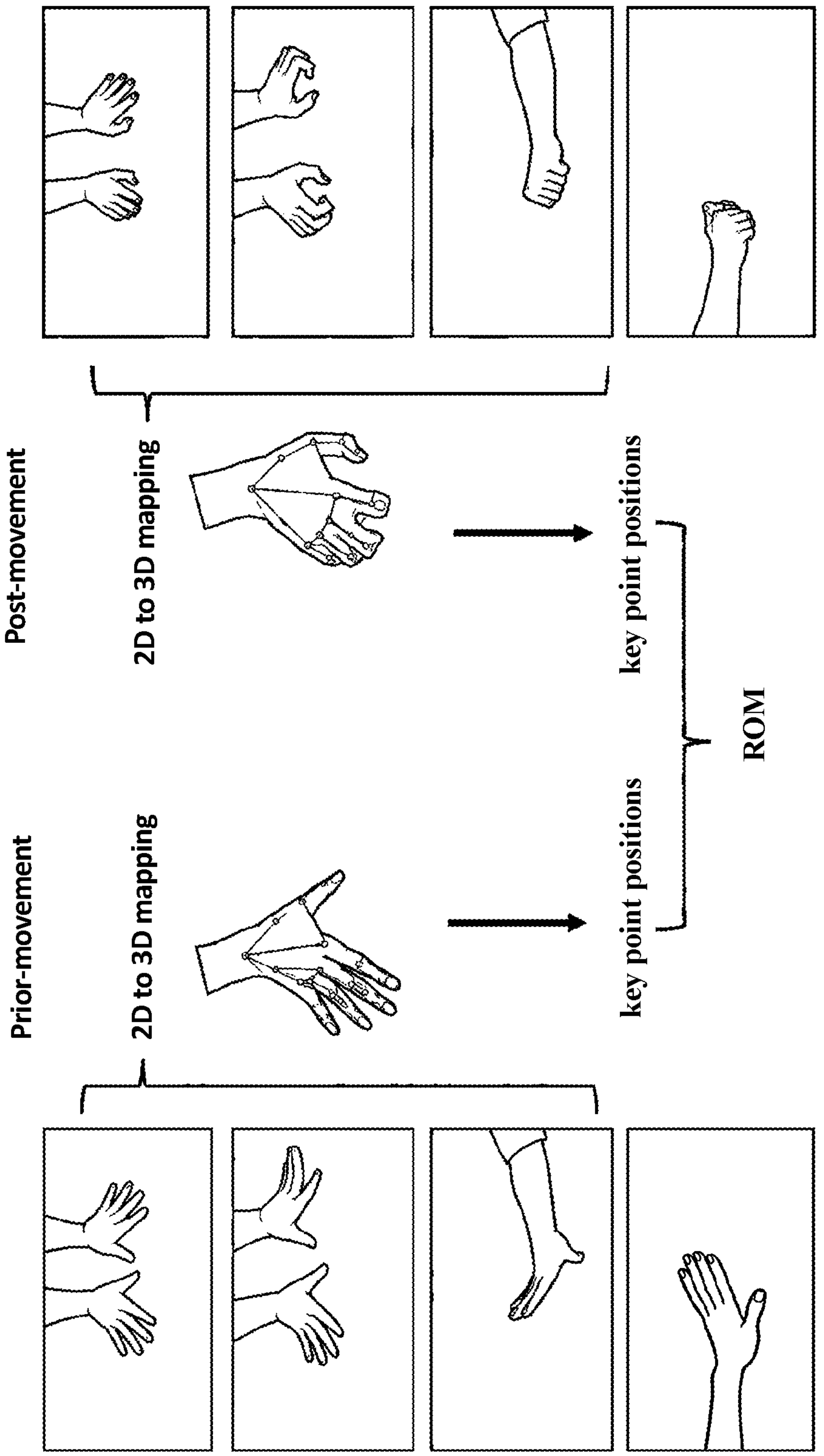
FIG. 3 shows more details on how prior-movement/post movement key point positions are obtained for calculating range of motion.

Referring to FIG. 3, in various embodiments, the plurality of prior-movement key point positions is obtained by mapping 2D positions of a plurality of sampling points of the hand in the prior-movement images into the projection 3D space through the camera matrixes to obtain a plurality of 3D prior-movement key point positions; and projecting the plurality of 3D prior-movement key point positions on a projection plane to obtain the plurality of prior-movement key point positions.

Similarly, the plurality of post-movement key point positions is obtained by mapping 2D positions of the plurality of sampling points of the hand in the post-movement images into the 3D space through the camera projection matrixes to obtain a plurality of 3D post-movement key point positions; and projecting the plurality of 3D post-movement key point positions on the projection plane to obtain the plurality of post-movement key point positions.

Figure 4:
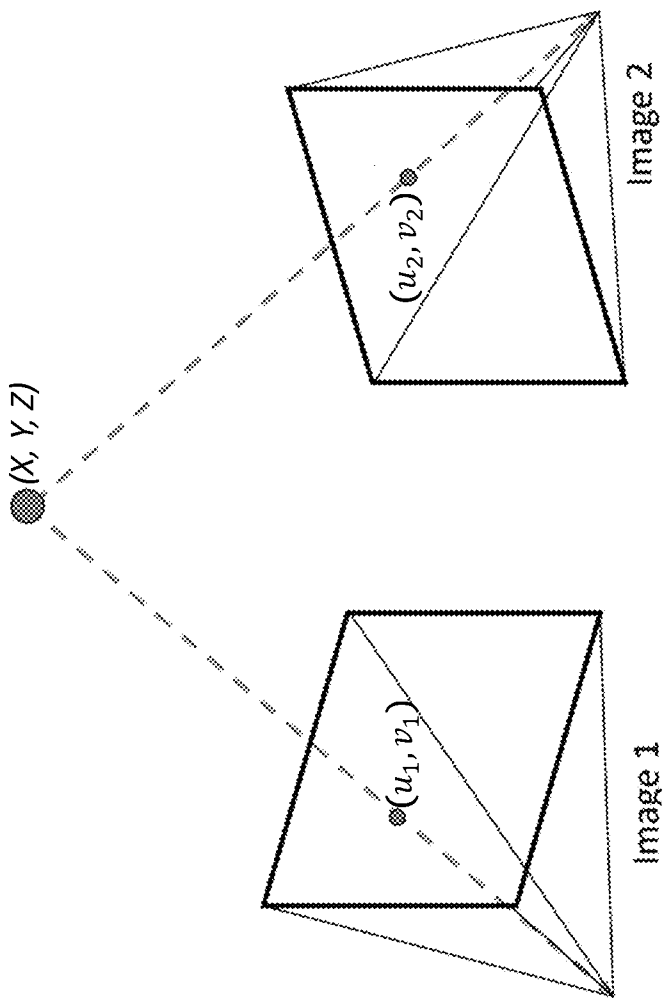
FIG. 4. shows how mapping of 2D positions from the prior-movement/post-movement images into the 3D space can be regarded as a triangulation problem.

Referring to FIG. 4, the mapping of 2D positions from the prior-movement/post-movement images into the 3D space can be regarded as a triangulation problem referring to a reverse process of camera projection which involve reconstruction of the coordinates of a point X in the 3D space given the camera projection matrix and the pixel coordinates $(u_1,v_1)$ and $(u_2,v_2)$ of imaged points in the images captured by the corresponding cameras.

In practical computations, the projection lines of the two cameras might not exactly intersect. Therefore, for multi-view images captured by multiple cameras respectively, the 2D to 3D mapping can be formulated as an optimization problem of minimizing the reprojection error:

$$\min\sum_{i}^{n}\|P_iX - x_i\|^2,$$

where n represents number of view angles (or cameras), i denotes the i-th camera, $P_i$ represents the projection matrix of the i-th camera, and $x_i=(u_i,v_i)$ represents the pixel coordinates of the imaged point in the i-th view angel, and X represents the desired coordinates of the object point.

Figure 5B:
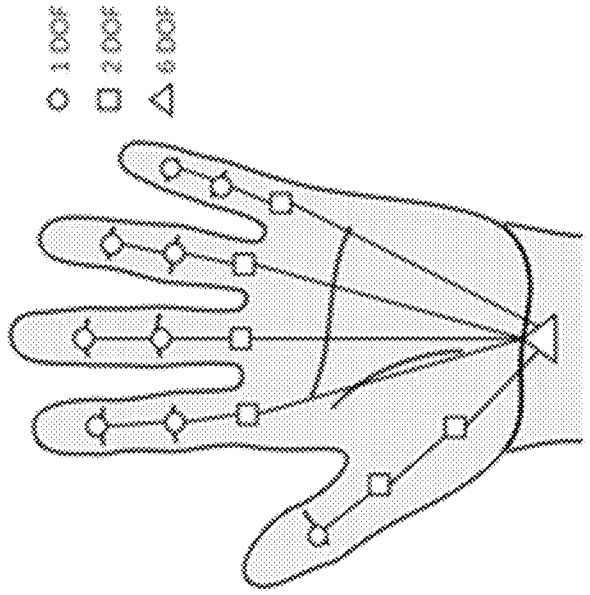
FIG. 5A shows an anatomical model of the hand and FIG. 5B shows a kinematic model used in determining the range of motion.
Figure 5A:
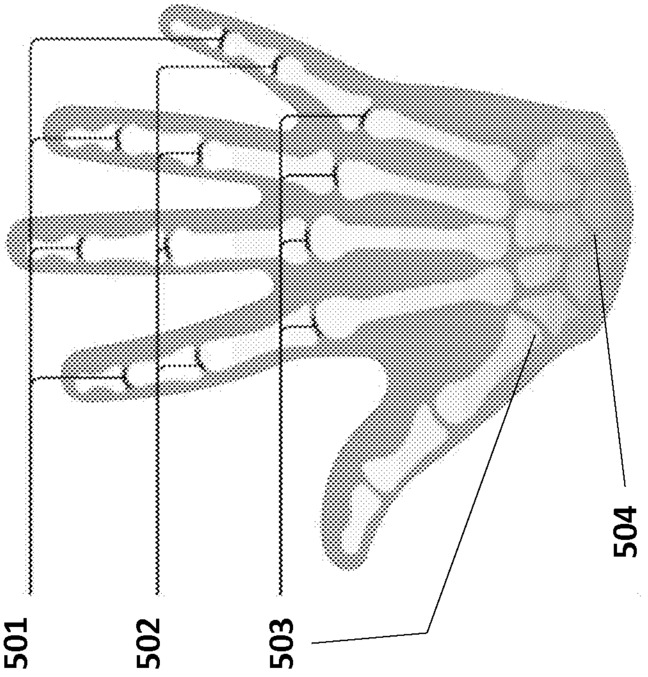

In some embodiments, the hand movement is designed with respect to a kinematic model of the hand. By analyzing the anatomical model (as shown in FIG. 5A) of the hand, the kinematic model of the hand can be obtained. Referring to FIG. 5A, distal interphalangeal (DIP) joints 501 and proximal interphalangeal (PIP) joints 502 are collectively referred to as interphalangeal joints. Each of the four fingers has two interphalangeal joints, while the thumb has only one interphalangeal joint. The interphalangeal joints are hinge joints, allowing only flexion and extension movements with one degree of freedom (DOF).

The metacarpophalangeal (MCP) joint 503, also known as the knuckle joint, is a ball-and-socket joint, allowing flexion/extension and abduction/adduction movements with two DOF. However, in clinical assessments, based on the assumption that the abduction/adduction of the MCP joint of the thumb is associated with the abduction/adduction of the carpometacarpal (CMC) joint 504 of the thumb, only flexion and extension evaluations (one DOF) are usually performed for the MCP joint of the fingers.

The CMC joint 504 is the carpometacarpal joint of the thumb, also known as TM joint, and it is a saddle joint, enabling flexion, extension, abduction, adduction, and circumduction movements with two DOF. Therefore, in the present invention, a 26 DOF kinematic model for the hand as shown in FIG. 5B is employed.

FIGS. 6A to 6G illustrate seven hand movements respectively designed for hand function assessment.

Figure 6A:
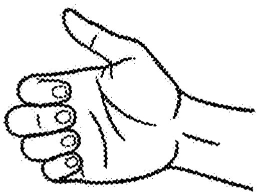
FIGS. 6A to 6G show seven hand movements respectively designed for hand function assessment.

Movement A (as shown in FIG. 6A) requires the subject to first extend all five fingers and then forcefully flex them to the maximum extent, is designed for demonstrating the flexion/extension range of motion of the nine interphalangeal joints in the hand.

Figure 6B:
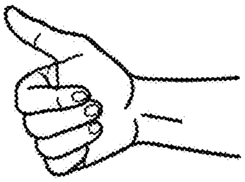

Movement B (as shown in FIG. 6B) requires the subject to keep the distal interphalangeal joints of the four fingers extended to form a straight first and then touch the fingertips as far as possible to the wrist. Movement B displays the flexion/extension range of motion of the four metacarpophalangeal joints in the hand.

Figure 6C:
Figure 6D:
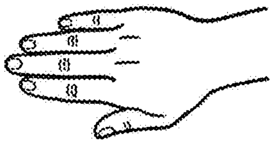

Movements C and D (as shown in FIGS. 6C and 6D respectively) involve the abduction and adduction of the four metacarpophalangeal joints respectively. The subject is required to fully spread the fingers apart and then bring them together to the maximum extent, the range of motion for finger abduction/adduction can then be assessed.

Figure 6E:
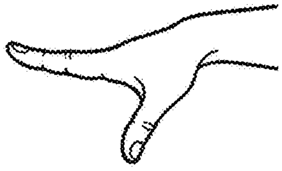
Figure 6F:
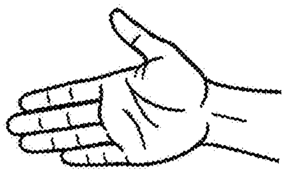

Movements E and F (as shown in FIGS. 6E and 6F respectively) involve abduction and adduction of the thumb carpometacarpal joint, including palmar abduction (E) and radial abduction (F).

Figure 6G:
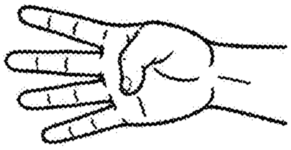

Movement G (as shown in FIG. 6G) requires the subject to relax the four fingers while fully flexing the thumb to the maximum extent. This movement demonstrates the maximum flexion of the thumb interphalangeal joint and metacarpophalangeal joint.

These specific movements are designed to assess the various ranges of motion of different joints in the hand, allowing therapists to evaluate the hand's flexibility, stability, and functionality of each joint in the hand. This assessment is common in clinical practice, especially for patients undergoing hand rehabilitation after injuries, hand diseases, or hand surgeries. Such assessments can also be used in research involving patients with hand diseases or movement disorders to understand how different conditions affect the range of motion in hand joints, providing a more scientific basis for treatment and rehabilitation strategies.

Figure 7:
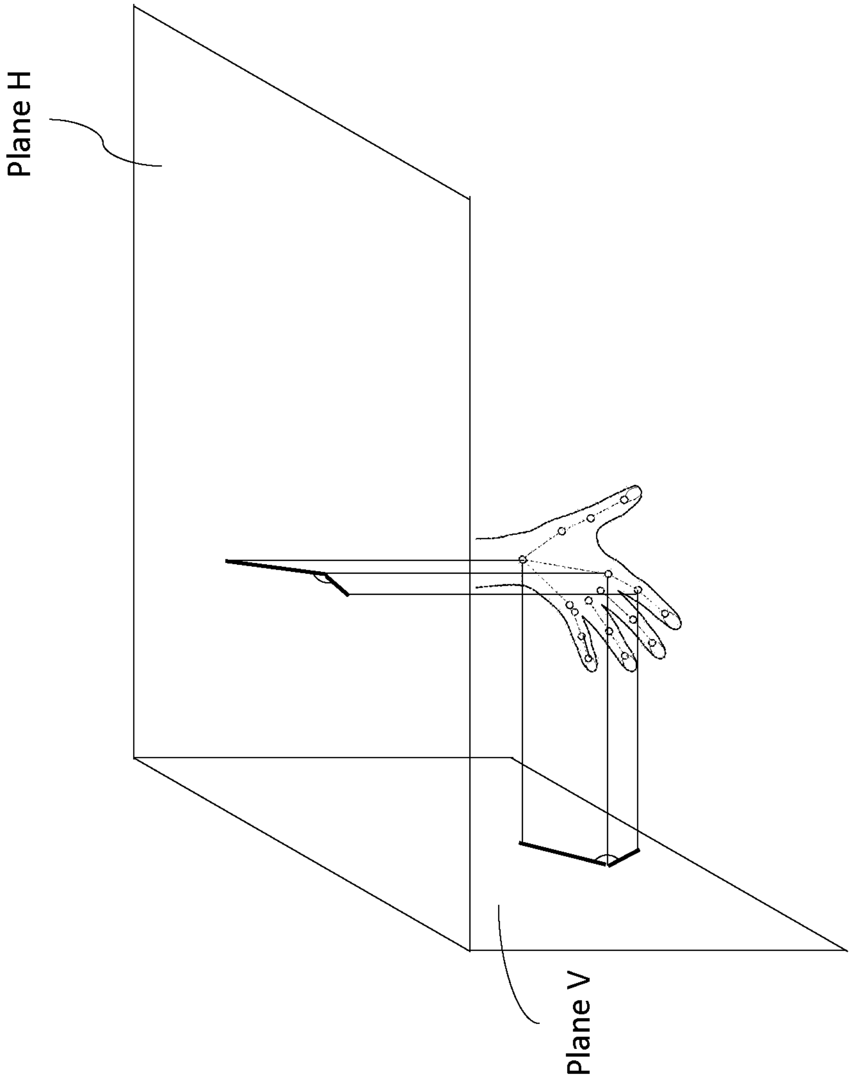
FIG. 7 shows how a plurality of 3D post-movement key point positions is projected on a plane perpendicular to the palm plane or a plane in parallel with the palm plane to obtain the plurality of post-movement key point positions for calculating the ROM.

Referring to FIG. 7, depending on the declination angles of joints to be measured in determining the range of movement, the projection plane may be a plane H in parallel with a palm plane of the hand and/or a plane V perpendicular to the palm plane. The projected prior-movement key point positions and post-movement key point positions are then used to calculate the ROM.

For example, for movements A, B and E, the plurality of 3D post-movement key point positions is projected on the plane perpendicular to the palm plane to obtain the plurality of post-movement key point positions for calculating the ROM. For movements C, D, F and G, the plurality of 3D post-movement key point positions is projected on the plane in parallel with the palm plane to obtain the plurality of post-movement key point positions for calculating the ROM.

The embodiments were chosen and described in order to best explain the principles of the invention and its practical application, thereby enabling others skilled in the art to understand the invention for various embodiments and with various modifications that are suited to the particular use contemplated. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations. While the apparatuses disclosed herein have been described with reference to particular structures, shapes, materials, composition of matter and relationships . . . etc., these descriptions and illustrations are not limiting. Modifications may be made to adapt a particular situation to the objective, spirit and scope of the present disclosure. All such modifications are intended to be within the scope of the claims appended hereto.

The invention claimed is:

1. A machine vision-based method for determining a range of motion of a joint of a hand of a subject, comprising:

facilitating the subject to perform a hand movement at a preset position;

calibrating each of at least two cameras, which are configured to capture images of the hand from at least two perspectives respectively, with respect to a 3D space to obtain a respective camera projection matrix;

capturing, by the at least two cameras, at least two prior-movement images of the hand when the hand is in a neutral posture before performing the hand movement;

capturing, by the at least two cameras, at least two post-movement images of the hand when the hand is in an assessment posture after performing the hand movement;

processing, using a neural network, the captured prior-movement images to obtain a plurality of prior-movement key point positions;

processing the captured post-movement images to obtain a plurality of post-movement key point positions; and calculating the range of motion of the joint based on the plurality of prior-movement key point positions and the plurality of post-movement key point positions; and wherein the plurality of prior-movement/post-movement key point positions is obtained by mapping 2D positions of a plurality of sampling points of the hand in the prior-movement/post-movement images into the 3D space through the camera projection matrixes to obtain a plurality of 3D prior-movement/post-movement key point positions; and projecting the plurality of 3D prior-movement/post-movement key point positions on one or more projection planes to obtain the plurality of prior-movement/post-movement key point positions;

wherein the plurality of 3D prior-movement/post-movement key point positions is optimized by formulating the mapping the 2D positions of the plurality of sampling points of the hand in the prior-movement/post-movement images into the 3D space as an optimization of minimizing reprojection error using a neural network;

wherein the one or more projection planes include a plane in parallel with a palm plane of the hand and a plane perpendicular to the palm plane;

wherein the plurality of sampling points of the hand includes:

finger tips, distal interphalangeal (DIP) joints, proximal interphalangeal (PIP) joints, metacarpophalangeal (MCP) joints of the four fingers; and interphalangeal (IP) joint, metacarpophalangeal (MCP) joint, and carpometacarpal (CMC) joint of the thumb;

wherein the hand movement is designed by employing a kinematic model presuming a plurality of degrees of freedom of the hand; and wherein the plurality of presumed degrees of freedom of the hand includes:

flexion and extension movements of the distal interphalangeal (DIP) joints and the proximal interphalangeal (PIP) joints of the four fingers;

flexion, extension, abduction, adduction, and circumduction movements of the metacarpophalangeal (MCP) joints of the four fingers;

flexion and extension movements of the interphalangeal (IP) joint and the metacarpophalangeal (MCP) joint of the thumb; and palmar abduction, and radial abduction of the carpometacarpal (CMC) joint of the thumb.

2. A machine vision-based system for determining a range of motion of a joint of a hand of a subject, the system comprising:

a supporter configured to facilitating the subject to perform a hand movement at a preset position;

at least two cameras configured to:

capture at least two prior-movement images of the hand when the hand is in a neutral posture before performing the hand movement; and capture at least two post-movement images of the hand when the hand is in an assessment posture after performing the hand movement; and a processor configured to:

calibrate each of the at least two cameras with respect to a 3D space to obtain a respective camera projection matrix;

process the captured prior-movement images to obtain a plurality of prior-movement key point positions;

process the captured post-movement images to obtain a plurality of post-movement key point positions; and calculate the range of motion of the joint based on the plurality of prior-movement key point positions and the plurality of post-movement key point positions; and wherein the plurality of prior-movement/post-movement key point positions is obtained by mapping 2D positions of a plurality of sampling points of the hand in the prior-movement/post-movement images into the 3D space through the camera projection matrixes to obtain a plurality of 3D prior-movement/post-movement key point positions; and projecting the plurality of 3D prior-movement/post-movement key point positions on one or more projection planes to obtain the plurality of prior-movement/post-movement key point positions;

wherein the plurality of 3D prior-movement/post-movement key point positions is optimized by formulating the mapping the 2D positions of the plurality of sampling points of the hand in the prior-movement/post-movement images into the 3D space as an optimization of minimizing reprojection error using a neural network wherein the one or more projection planes include a plane in parallel with a palm plane of the hand and a plane perpendicular to the palm plane;

wherein the plurality of sampling points of the hand includes:

finger tips, distal interphalangeal (DIP) joints, proximal interphalangeal (PIP) joints, metacarpophalangeal (MCP) joints of the four fingers; and interphalangeal (IP) joint, metacarpophalangeal (MCP) joint, and carpometacarpal (CMC) joint of the thumb;

wherein the hand movement is designed by employing a kinematic model presuming a plurality of degrees of freedom of the hand; and wherein the plurality of presumed degrees of freedom of the hand includes:

flexion and extension movements of the distal interphalangeal (DIP) joints and the proximal interphalangeal (PIP) joints of the four fingers;

flexion, extension, abduction, adduction, and circumduction movements of the metacarpophalangeal (MCP) joints of the four fingers;

flexion and extension movements of the interphalangeal (IP) joint and the metacarpophalangeal (MCP) joint of the thumb; and palmar abduction, and radial abduction of the carpometacarpal (CMC) joint of the thumb.

3. A non-transitory computer-readable storage medium storing a program including instructions for performing the machine vision-based method of claim 1.

* * * * *